United States Patent
Doane et al.

(10) Patent No.: US 11,738,187 B2
(45) Date of Patent: Aug. 29, 2023

(54) CONTINUOUS TUBING WITH ALTERNATING COMPOSITIONS FOR MEDICAL DEVICES

(71) Applicant: CareFusion 303, Inc., San Diego, CA (US)

(72) Inventors: Mark W. Doane, San Diego, CA (US); Wan Suwito, San Diego, CA (US); Anthony Guevara, San Diego, CA (US); Archana Nagaraja Rao, San Diego, CA (US); Zehra Sevinc, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 304 days.

(21) Appl. No.: 16/785,306

(22) Filed: Feb. 7, 2020

(65) Prior Publication Data

US 2021/0244931 A1    Aug. 12, 2021

(51) Int. Cl.
A61M 25/00    (2006.01)
A61M 39/10    (2006.01)
A61L 29/08    (2006.01)
A61L 29/14    (2006.01)

(52) U.S. Cl.
CPC ........... *A61M 39/10* (2013.01); *A61L 29/085* (2013.01); *A61L 29/141* (2013.01); *A61M 25/0053* (2013.01)

(58) Field of Classification Search
CPC .......... A61M 25/0053; A61M 25/0054; B29C 48/16; B29C 48/22; B29C 48/18; B29C 48/022
See application file for complete search history.

(56) References Cited

U.S. PATENT DOCUMENTS

| | | | |
|---|---|---|---|
| 3,690,798 A | 9/1972 | Brukovsky et al. | |
| 2005/0142314 A1* | 6/2005 | Burgmeier | A61L 29/14 |
| | | | 264/211 |
| 2012/0150125 A1 | 6/2012 | Karlsson et al. | |

FOREIGN PATENT DOCUMENTS

| | | |
|---|---|---|
| CA | 2547874 A1 | 6/2005 |
| EP | 0380102 A1 | 8/1990 |
| GB | 1226672 A | 3/1971 |
| WO | WO-2017127074 A1 | 7/2017 |

OTHER PUBLICATIONS

International Search Report and Written Opinion for Application No. PCT/US2021/016672, dated May 19, 2021, 14 pages.
International Preliminary Report on Patentability from the International Preliminary Examining Authority for Application No. PCT/US2021/016672, dated Apr. 25, 2022, 17 pages.
Written Opinion from the International Preliminary Examining Authority for Application No. PCT/US2021/016672, dated Jan. 24, 2022, 7 pages.

* cited by examiner

*Primary Examiner* — Deanna K Hall
(74) *Attorney, Agent, or Firm* — Morgan, Lewis & Bockius LLP

(57) ABSTRACT

A continuous tube having alternating compositions along a length direction of the tube can include at least a first segment extruded from a first composition along a length direction of the tube and at least a second segment extruded from a second composition along the length direction of the tube in which the first and second segments are integrally joined. Additional segments can be added to the continuous tubing. Such tubing can be used as medical device such as with infusion sets.

12 Claims, 3 Drawing Sheets

CONTINUOUS TUBING WITH ALTERNATING COMPOSITIONS FOR MEDICAL DEVICES

TECHNICAL FIELD

The present disclosure generally relates to tubing and, in particular, to continuous tubing that has alternating compositions along a length direction. Such tubing can be used for medical devices such as tubing for administration of medical fluid by infusion.

BACKGROUND

Plastic tubing is extensively used in the medical field, particularly for patient analysis and treatment procedures. However, different and sometimes incompatible demands are required for medical tubing. For example, medical tubing should be inert and avoid contamination of fluid transported there through. But many plastic materials that have such characteristics tend to be inflexible. In many applications, however, medical tubing is pinched or clamped or used with infusion pumps that move fluid through the tubing by compressing the tubing. Such uses require the tubing to be flexible. However, soft tubing such as silicone is difficult to join to other materials such as polycarbonate, PMMA, acrylic terpolymers, polyester, co-polyesters, acrylonitrile-butadiene-styrene and methacrylic acrylonitrile-butadiene-styrene based connectors.

To address the differing demands paced on medical tubing, such tubing has been made with multiple layers of differing polymeric materials to change the characteristics of the tubing. However, tubing made of different materials can suffer from delamination. Mechanical and friction joining of flexible tubing has also been used but such mechanisms have limited low pull force and the tubing can slip through the mechanical holding mechanisms. Hence, a continuing need exists for medical tubing that can address differing demands of medical applications.

SUMMARY

Aspects of the subject technology relate to continuous tubing having alternating compositions along a length direction of the tube. Such a continuous tube can include at least a first segment with a first composition along a length direction of the tube and at least a second segment with a second composition along the length direction of the tube in which the first composition is different from the second composition. The tube can include additionally a third, fourth, etc. segment with the same or different compositions. The segments are integrally joined and can be formed by sequential extrusion of a first composition followed by extrusion of a second composition, etc.

The subject technology also relates to a method of forming a continuous tube having alternating compositions along a length direction of the tube. The method can include extruding a first segment of a tube from a first composition along a length direction of the tube by a first pump on an extrusion line followed by extruding a second segment of the tube from a second composition along the length direction of the tube by a second pump on the extrusion line. Advantageously, the first and second composition are different and the first segment and second segments are integrally joined by the sequential extrusion of the first and second compositions to for the respective segments. The method can also include extruding a third segment of the tube from a third composition along the length direction of the tube by a third pump on the extrusion line in which the second segment and third segments are integrally joined. In some aspects, the method further includes forming a transition segment between adjoining segments, e.g., forming a transition segment between the first and second segment. The transition segment comprises a mixture of the respective compositions forming the adjoining segments.

Embodiments of the foregoing continuous tubing and methods include one or more of the following features individually or combined. In some embodiments, the first composition can be different from the second composition such that a property of the first segment and second segment differs by a level of at least 5%. For example, the first and second segments can have Shore A hardness levels that differ by at least 5% as the property that differs. Such difference in a property can be achieved by differing the polymeric material in the first and second composition and/or by differing an amount or type of an additive between the first and second composition. For example, the first segment can comprise a polyvinyl chloride composition with an amount of a plasticizer and the second segment can comprise a polyvinyl chloride composition with an amount of a plasticizer in which the amount of plasticizer in the first segment is less than the amount of plasticizer in the second segment. In other embodiments, the first segment, and optionally third segment, can have a Shore A hardness of at least about 70 and the second segment can have a Shore A hardness of no more than about 60. In still further embodiments, the first composition comprises a first polymer and the second composition comprises a second polymer in which the first polymer is different from the second polymer. In other embodiments, the composition of the first segment, and optionally third segment, can comprise a non-hydrogenated styrenic based TPE and the composition of the second segment can comprises a hydrogenated styrenic TPE.

Additional advantages of the subject technology will become readily apparent to those skilled in this art from the following detailed description, wherein only certain aspects of the subject technology are shown and described, simply by way of illustration. As will be realized, the subject technology is capable of other and different configurations, and its several details are capable of modifications in various other respects, all without departing from the subject technology. Accordingly, the drawings and description are to be regarded as illustrative in nature, and not as restrictive.

BRIEF DESCRIPTION OF THE DRAWINGS

The accompanying drawing, which is included to provide further understanding and is incorporated in and constitute a part of this specification, illustrate disclosed embodiments and together with the description serve to explain the principles of the disclosed embodiments. In the drawings.

DETAILED DESCRIPTION

Figure 1:
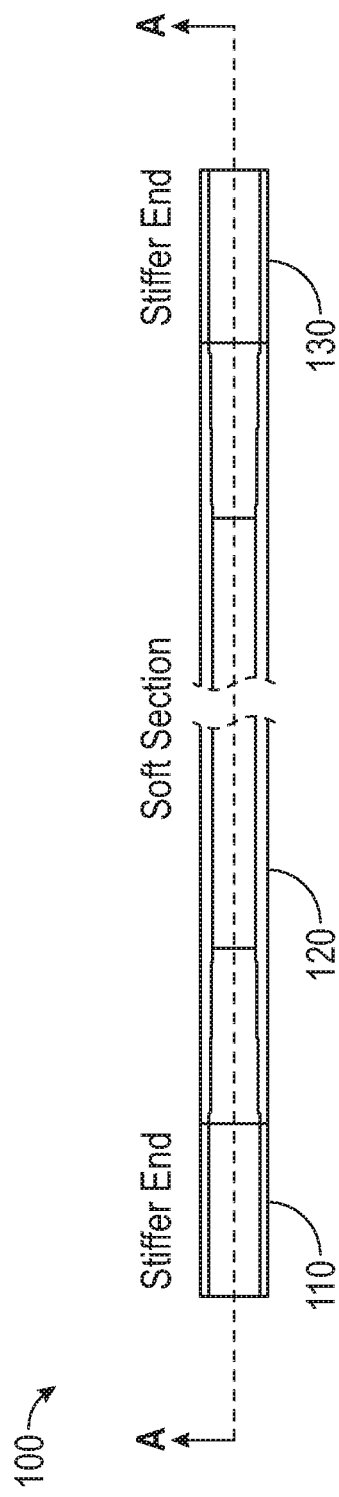
FIG. 1 illustrates an exemplary continuous tube with alternating compositions along a length direction that manifests in hard-soft-hard segments along the tube length.

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Aspects of the subject technology relate to continuous tubing having alternating compositions along a length direction of the tube and, in particular, to a continuous tube having at least a first segment formed of a first composition along a length direction and at least a second segment formed of a second composition along the length direction of the tube in which the first composition is different from the second composition thus forming an A-B segmented continuous tube, in which "A" and "B" represent segments formed of different compositions. Advantageously, the first and second segments are integrally joined to each other along the length direction of the tube with or without a transition segment.

In certain aspects of the present disclosure, continuous tubing having alternating first and second segments can further include other segments, e.g., a third segment along the length direction of the tube integrally joined to the second segment. The third segment can be formed of a third composition such that the first and third segments are composed of different materials thus forming an A-B-C segmented continuous tube. Alternatively, the first and third segments can be formed from the same composition thus forming an A-B-A segmented continuous tube. Advantageously, adjacent segments of different compositions are integrally joined, e.g., the first and second segments are integrally joined to each other and the second and third segments, etc. are integrally joined to each other with or without a transition segment.

In certain aspects of the present disclosure, the compositions that are different from another, e.g., the first and second compositions, form segments that can have a property, e.g., hardness, flexibility, bondability, that differ by a level of at least 5%, such as at least 10%. For example, adjoining segments can have a hardness that differ by a level of at least 4 units. Alternatively, adjoining first and second segments can have Shore A hardness levels that differ by at least 5%. In some aspects of the present disclosure, the first segment of a continuous tubing can be rigid or hard while an integrally joined second segment can be soft. Medical tubing for IV sets having a Shore A hardness above about 85 is considered rigid, for example, and used for certain applications while tubing used with pumping medicinal fluids typically employs softer tubing with a Shore A hardness of about 60 or less, for example. In in some aspects of the present disclosure, hard-soft segments can be integrally joined in which the hard segment is formed of a first composition and the soft segment is formed of a second composition. The first and second compositions can include the same or different polymers. When including the same polymers, such as polyvinylchloride, the first and second compositions include different amounts or types of additives, such as a lower or higher amount of a plasticizer, thus forming different compositions. In other aspects of the present disclosure, the first and second segments can have the same or similar hardness levels but comprise different polymers.

The alternating continuous tubing of the present disclosure can be manufactured by alternate extrusion of differing compositions on the same extrusion line. For example, an extrusion line having a first extrusion pump fed with a first composition can be activated to extrude a first segment of a tube made with the first composition and, after a certain length, the first pump can be deactivated. A second pump fed with a second composition can then be activated to extrude a second segment of the tubing with the second composition for a certain length and then the second pump can be deactivated. The process can be repeated by activating and deactivating the first and second pumps with the first and second compositions, respectively, to form a tube having alternating first and second segments with first and second compositions. Alternating tubing formed by alternate extrusion can be cut within a first segment or within second segment to form tubing having an A-B-A or B-A-B segmentation. In addition, yet additional extrusion pumps feeding yet different compositions can also be included on the same extrusion line to form third, fourth, etc. segments with third, fourth etc. compositions and in any order. Tubing made on an alternate polymer extrusion line can have a material transition section where different compositions are mixed and the mixture forms the transition segment between a first and second segment, for example. A transition segment can be due to a small volume of one composition remaining in a dead space between a pump and a die exit area on an extrusion line when one of the composition pumps, e.g., a first pump, stops and another pump starts, e.g., a second pump. This material transition section can be minimized by reversing a pump before it is to be stopped. Alternatively, or in addition thereto, a transition segment between segments, e.g. between a first and second segment, can be minimized by draining a composition in the dead space with a vale.

Hence, in an aspect of the present disclosure, a method of forming a tube having alternating compositions along a length direction of the tube includes extruding a first segment of a tube along a length direction of the tube from a first composition by a first pump on an extrusion line followed by extruding a second segment of the tube along the length direction of the tube from a second composition by a second pump on the extrusion line. By sequential extrusion of the first and second segments, the first segment and second segments are integrally joined. The method can also include extruding a third segment of the tube from a third composition along the length direction of the tube by a third pump on the extrusion line to integrally join the second and third segments. The first, second and third compositions can be different and can give rise to segments with a property, e.g., hardness, that differs by a level of at least 5% such as at least 10%.

The alternate extrusion technology used to prepare tubing having alternating compositions along a length direction of the tube advantageously can make essentially seamless transitions between the various segments since the segments are integrally joined. The transitions between segments are thus as strong as about the materials compositions themselves. Further the method can include forming a transition segment between adjoining segments, e.g., between a first segment and a second segment in which the transition segment comprises a mixture of the first and second composition. Alternatively, such a transition segment can be minimized by reversing a pump associated with a particular segment.

Selection of different compositions for the different segments of the continuous tubing that are somewhat miscible facilitate integration of the compositions along the tube and resist separation of the first, second, etc. segment of the tube made from such different compositions. Miscibility computations from Hansen Solubility Parameters and/or literature can be used as a guide for selecting suitably miscible materials and compositions thereof. Such information can be found in, for example, White, James L. Kim, Kwang-Jea. (2008). *Thermoplastic and Rubber Compounds—Technology and Physical Chemistry*—5.4 *Miscible Polymer Blends*. (pp. 157, 158, 159). Hanser Publishers.

For example, compositions that can be sequentially extruded as a first composition includes a styrenic based thermoplastic elastomers (TPE), non-hydrogenated styrenic based TPE, thermoplastic polyurethane ester based, ether based or carbonate based, thermal plastic olefin (TPO) or combinations thereof, TPO blend with low density polyethylene (LDPE) or polypropylene (PP), Polyether block amide, copolyester elastomers, polyvinyl chloride (PVC) and any blend thereof. Compositions that can be sequentially extruded as a second composition include, for example, styrenic based TPE, non-hydrogenated and hydrogenated styrenic based TPE and blends thereof, Thermoplastic polyurethane ester based, ether based, or carbonate based, EVA, EVA blend with a thermoplastic polyurethane (TPU), polyethylene vinyl acetate (EVA) blend with LDPE, TPO, PVC, etc. and combinations thereof. TPO, a thermal plastic olefin includes: Propylene based elastomer, Olefin block copolymers, propylene-ethylene copolymers, ethylene octane copolymer. Styrenic based TPE includes hydrogenated polyisoprene polymers like styrene-ethylene propylene styrene (SEPS), styrene-ethylene propylene (SEP), hydrogenated polybutadiene polymers like styrene-ethylene butylene-styrene (SEBS), styrene-ethylene butylene (SEB), styrene butadiene-styrene (SBS), styrene-isoprene-styrene (SIS), styrene-isoprene-butadiene-styrene (SIBS), hydrogenated poly isoprene/butadiene polymer like styrene-ethylene ethylene propylene-styrene (SEEPS), and the blends thereof with polyolefin such as polypropylene. The first and second, and optionally third, compositions can include additives such as plasticizers.

FIG. 1 illustrates an example of a continuous tube having alternating compositions along a length direction as an A-B-A segmented continuous tube. As depicted, continuous tube 100 includes first and third segments (110, 130, respectively) on opposite ends of tube 100 and middle segment 120. First and third segments (110, 130, respectively) can be extruded from a first composition and integrally joined to middle segment 120 which can be extruded from a second composition. For this example, end segments (110 and 130) comprise a composition that results in a hard segment and a middle segment (120) is comprised of a composition that forms a comparatively soft segment. For example, first and third segments can have a Shore A hardness of greater than about 85 and second segment can have a Shore A hardness of less than about 80 Hardness of Shore A greater than about 85 for medical tubing application is typically considered hard. Pump tubing typically employs softer tubing at about 55 Shore A. The tubing above 85 Shore A is considered rigid. For this example, end segments 110 and 130 are of a relatively shorter length than middle segment 120, e.g., end segments (110, 130) have a length of no more than about 2 inches (about 50.8 mm) such as between about 0.25 inches (6.35 mm) and about 1.5 inches (38.1 mm). Such an A-B-A segmented tube can be used for solvent bonding the A segments to connectors such as pocket joints of connectors comprising rigid acrylic-based materials. In this way, tubes made of materials that are difficult to solvent bond (e.g., segment 120) can be solvent bonded by the end segments (110, 130), which can be made of materials that more readily solvent bond to connectors.

Figure 2:
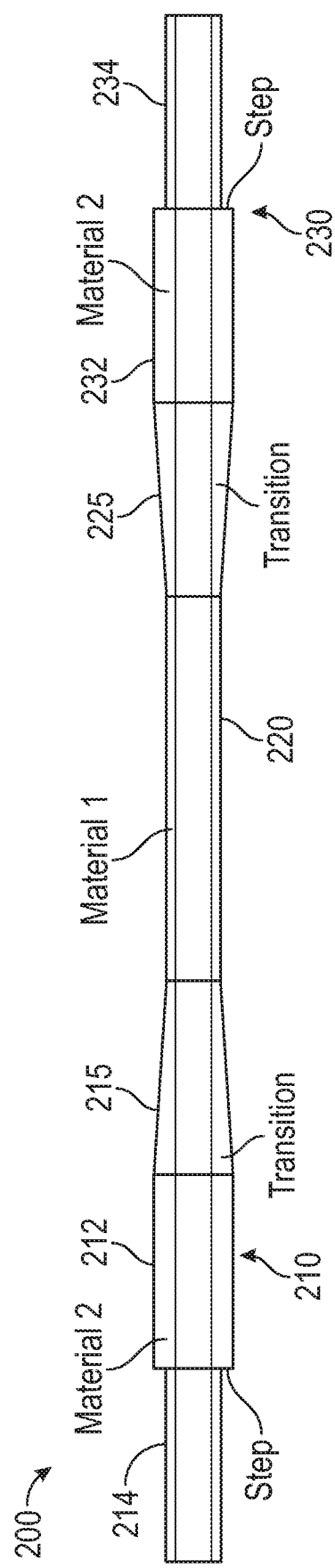
FIG. 2 illustrates another exemplary continuous tube with alternating compositions along a length direction that manifests in hard-soft-hard segments along the tube length. For this example, the tube is stepped down to a smaller outer diameter at either ends of the tube, which can be helpful for determining placement of the ends in pocket joints of a connector.

FIG. 2 illustrates another exemplary continuous tube with alternating compositions along a length direction that manifests in hard-soft-hard segments along the tube length. As depicted, continuous tube 200 includes first and third segments (210, 230, respectively) on opposite ends of tube 200 and middle segment 220. For this example, end segments (210 and 230) comprise a composition that results in a hard segment and a middle segment (220) is comprised of a composition that forms a comparatively soft segment. First and third segments (210, 230, respectively) can be extruded from a first composition and integrally joined to middle segment 220 which can be extruded from a second composition. For this example, tube 200 includes transition segment 215 between first segment 210 and second segment 220, which can be formed by alternative extrusion technology as described herein and transition segment 225 between second segment 220 and third segment 230. Transitions segments (215, 225) are less than about 15 mm in length. In addition, first segment 210 includes a first diameter segment (212) and a stepped-down (smaller) diameter segment (214) and third segment 230 includes a first diameter segment (232) and a stepped-down (smaller) diameter segment (234). The stepped-down diameter segments (214, 234) can be inserted in pocket joints of connectors such as connectors comprising rigid acrylic-based materials. Further, such a configuration can be used to visually inspect whether a joint is inserted completely.

Figure 3:
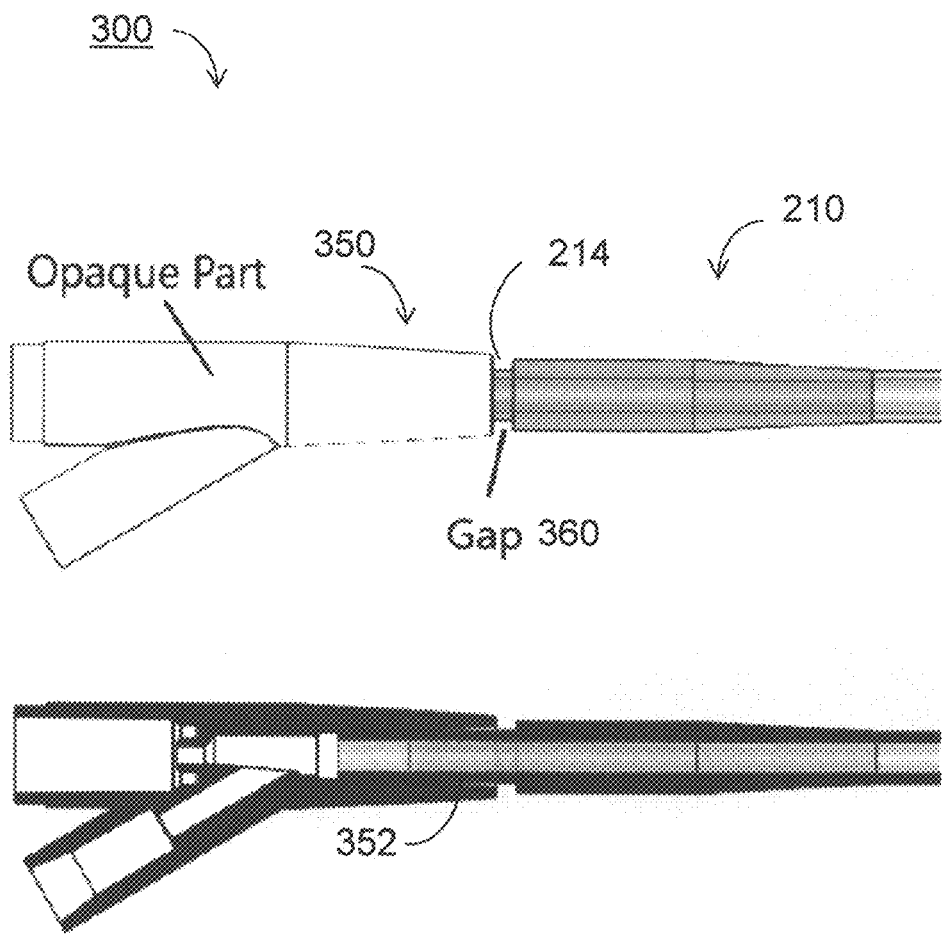
FIG. 3 illustrates an exemplary continuous tube with alternating compositions along a length direction inserted, in part, in a pocket of an exemplary connector.

FIG. 3 illustrates the exemplary continuous tube 200 with stepped-down (smaller) diameter segment (214) of first segment inserted, in part, in a pocket (352) of exemplary connector 350. If tube is not fully inserted into a pocket of a connector for bonding the tube to the connector, or if the tube should exit the pocket with force, due to, for example, lack of proper bonding with a solvent, then a gap (360) is apparent just outside the bond pocket entrance. A control measure can be put in place to monitor the presence of a gap and if a gap with certain predetermined length is found, the joint can be considered bad.

Continuous tubing of the present disclosure, such as exemplified in FIGS. 1-3, can be used as medical tubing for administration of medical fluid by infusion such as with intravenous assemblies, gravity containers and/or infusion pumps for the transport of intravenous fluid to a patient. An assembly of tubing, valves, fittings, and needles that connect a fluid container to a patient intravenously may be referred to as an "IV set". Infusion pumps are medical devices that may be used to administer intravenous (IV) fluids. Such assemblies, containers and pumps employ tubing bound to one or more medical connectors and tubing of the present disclosure is useful as such.

In certain aspects, continuous tubing can include a first and third segment, e.g., end segments of an A-B-A tube, formed from acrylic based TPE blends, non-hydrogenated styrenic thermoplastic elastomers, thermoplastic polyurethane, PVC and a second, e.g., middle segment, formed of a hydrogenated styrenic thermoplastic elastomer, a hydrogenated styrenic thermoplastic elastomer blend with PP, a blend of hydrogenated and non-hydrogenated styrenic thermoplastic elastomer, a polyvinyl chloride, a thermoplastic polyurethane, a Thermoplastic Silicone-Polyether-urethane An alternating continuous tubing designed by selection of suitable materials for various segments of the tubing such as end segments and a middle segment enables custom tailored tubing with properties that cannot be achieved by a tube formed from a single material or even laminated materials. An alternative extrusion technology (AET) as described herein allows custom tailored designs as shown in FIGS. 1-3, for example.

In addition, continuous tubing having alternating compositions along a length direction of the tube can be used in pump infusion sets. Pump infusion sets typically have tubing that is mounted to a pump to regulate the fluid flow. In some applications, the tube includes an upper fitment and lower fitment attached to opposite ends of the tube. The tube is generally made from soft polymers, e.g., silicone, to allow for compression with a relatively low force and to allow for a complete rebound of the tube once the force is removed. However, silicone tubing is difficult to join to other materials, such as, polycarbonate (PC), acrylonitrile-butadiene-styrene (ABS), acrylic and other plastics. Because of the difficulty of bonding silicone to other plastics, a mechanical/friction device is typically used to join silicone to other plastics such as the fitment using with pumps. These joining devices, however, typically result in a low pull force (about 3 lbf), i.e., the force needed to disconnect the silicone tube joined to another plastic. This is because, first, there is no inter molecular welding, and second since silicone is the softer material, it deforms easily.

Continuous tubes having alternating compositions along a length direction according to the present disclosure, however, can replace traditional silicone tubing joined with other plastics through mechanical/friction devices. Thus, continuous tubes having alternating compositions along a length direction according to the present disclosure can advantageously minimize the components needed for joining tubing to other devices.

Figure 4:
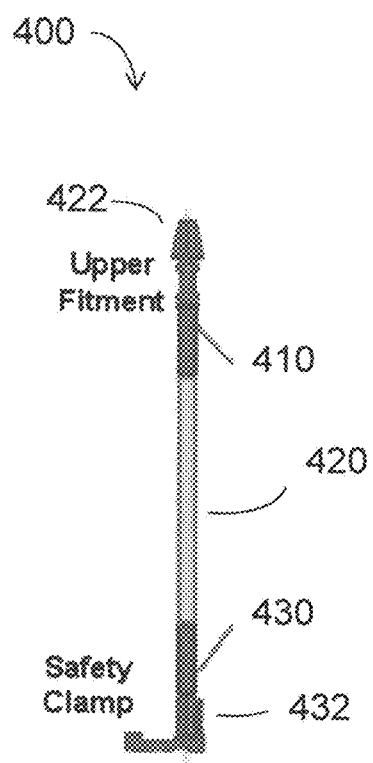
FIG. 4 illustrates another exemplary continuous tube, with alternating compositions along a length direction.

An example of a continuous tube with alternative segments of hard-soft-hard is shown in FIG. 4. As depicted, tube 400 has a first and third segment (410. 430, respectively) on opposite ends of the tube and a middle segment (420). For this example, end segments (410 and 430) comprise a composition that results in a hard segment, e.g., having a Shore A hardness of at least about 70A such as from 70A to about 85A, and, a middle segment (420) is comprised of a composition that forms a soft segment, e.g., having a Shore A hardness of no more than about 60A, such as between about 55A to 50A. Such a continuous tube can be formed from extruding alternating first and second compositions and cutting such a formed tube within the first segment formed of the first composition. Further, a tube having hard-soft-hard segments can be formed from a first composition comprising a hard PVC polymeric composition integrally joined through sequential extrusion to a middle segment formed from a softer PVC composition that has a durometer of about 50A to about 55A. The hard PVC polymeric composition used for the first segment can comprise a lower amount of plasticizer than the softer PVC polymeric composition used for the second segment. The middle segment of the hard-soft-hard segmented tube can match the softness of a silicone while having hard end segments available for boding to fitments.

In addition, the transition between segments can be seamless making the joining hard-soft-hard segments integral with one another and about as strong as the material compositions of the segments themselves. The end segments of such an integrally formed hard-soft-hard tube can be joined to an upper and lower fitment component (422, 432, respectively), by solvent bonding rather than by joining the fitment mechanically. As a result, the pull force is expected to be much higher (about 15 lbf or more) than a silicone mechanical joints.

In addition, continuous tubing having alternating compositions along a length direction of the tube can be used as medical devices such as catheter tubing. Certain conventional catheter tubing utilizes silicone with a lubricant coating on an end thereof prepared by a second process after forming the silicone tube. The lubricious coating is desired since such a coating more readily allows easy entry of the silicone catheter into delicate mucosal tissue. However, problems may arise with control of lubricant or coating amount, homogenous coverage over the tubing, and lowered effectiveness due to shearing during insertion, cost and complication from the secondary processes of applying a lubricious coating on to the catheter. Advantageously, the process described in the present disclosure can manufacture catheter tubing having a first segment that is a lubricious material formed from a composition of one or more polymers and lubricant additive such polymers include for example a thermoplastic urethane, a PVC, a Polyether block amide. Such polymer can be formulated with lubricous additives such as EveGlide, Mobilize, PEBASlide, ProPellS, among other. A second segment can be made from a second composition material typical for catheters such as a thermoplastic polyurethane (TPU), PVC, Polyether block amide or combinations thereof.

It is understood that any specific order or hierarchy of blocks in the methods of processes disclosed is an illustration of example approaches. Based upon design or implementation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such, term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject, matter that fails to satisfy the requirement of 35 U.S.C. § 101, 102, or 103, nor should they be interpreted in such a way.

What is claimed is:

1. A continuous tube having alternating compositions along a length direction of the tube, the tube comprising at least a first segment with a first polymeric composition along a length direction of the tube and at least a second segment with a second polymeric composition along the length direction of the tube;

wherein the at least first segment is integrally joined to the second segment along the length direction of the tube by a transition segment between the first and second segment that comprises a mixture of the first and second polymeric compositions;

wherein the first polymeric composition has a first polymer and the second polymeric composition has a second polymer in which the first polymer is different from the second polymer; and wherein first segment and the second segment have Shore A hardness levels that differ by at least 5%.

2. The continuous tube of claim 1, wherein the first and second segments have Shore A hardness levels that differs by at least 10%.

3. The continuous tube of claim 1, wherein the first segment comprises a polyvinyl chloride composition.

4. The continuous tube of claim 1, comprising a third segment with a third polymeric composition along the length direction integrally joined to the second segment by a transition segment between the second and third segment that comprises a mixture of the second and third polymeric compositions.

5. The continuous tube of claim 1, comprising a third segment with a third polymeric composition along the length direction integrally joined to the second segment by a transition segment between the second and third segment that comprises a mixture of the second and third polymeric compositions; wherein the first segment and third segment have essentially the same polymeric composition.

6. The continuous tube of claim 5, wherein the composition of the first and third segments comprise a non-hydrogenated styrenic based TPE and the composition of the second segment comprises a hydrogenated styrenic TPE.

7. The continuous tube of claim 5, wherein the first and third segments have a Shore A hardness of at least about 70 and second segment has a Shore A hardness of no more than about 60.

8. The continuous tube of claim 1, wherein the first composition comprises a lubricious polymer and the second composition comprises a thermoplastic polyurethane (TPU), polyvinyl chloride, polyether block amide or combinations thereof.

9. The continuous tube of claim 1, wherein the continuous tube is medical tubing for administration of medical fluid by infusion.

10. The continuous tube of claim 1, wherein the first composition includes a styrenic based thermoplastic elastomers (TPE), non-hydrogenated styrenic based TPE, thermoplastic polyurethane ester based, ether based or carbonate based, thermal plastic olefin (TPO), or combinations thereof.

11. The continuous tube of claim 1, wherein the second composition includes a styrenic based TPE, non-hydrogenated and hydrogenated styrenic based TPE and blends thereof, thermoplastic polyurethane ester based, ether based, or carbonate based, EVA, EVA blend with thermoplastic polyurethane (TPU), polyethylene vinyl acetate (EVA) blend with LDPE, TPO, PVC, etc. and combinations thereof.

12. The continuous tube of claim 1, wherein the first and second compositions include a different type or amount of an additive.

\* \* \* \* \*